US00PP26943P3

(12) United States Plant Patent
Lintott et al.

(10) Patent No.: US PP26,943 P3
(45) Date of Patent: Jul. 12, 2016

(54) ***GAILLARDIA* PLANT NAMED 'FANFARE CITRONELLA'**

(50) Latin Name: *Gaillardia×grandiflora*
Varietal Denomination: Fanfare Citronella

(71) Applicants: Keith George Lintott, Bognor Regis (GB); Charles Richard Read, Bognor Regis (GB)

(72) Inventors: Keith George Lintott, Bognor Regis (GB); Charles Richard Read, Bognor Regis (GB)

( * ) Notice: Subject to any disclaimer, the term of this patent is extended or adjusted under 35 U.S.C. 154(b) by 82 days.

(21) Appl. No.: 14/544,083

(22) Filed: Nov. 21, 2014

(65) Prior Publication Data

US 2015/0150179 P1 May 28, 2015

Related U.S. Application Data

(60) Provisional application No. 61/963,168, filed on Nov. 25, 2013.

(51) Int. Cl.
*A01H 5/02* (2006.01)

(52) U.S. Cl.
USPC ..... Plt./431

(58) Field of Classification Search
USPC ..... Plt./431
See application file for complete search history.

*Primary Examiner* — Annette Para
(74) *Attorney, Agent, or Firm* — Bethany R. Roahrig; Barbara Campbell; Cochran Freund & Young, LLC

(57) ABSTRACT

A new cultivar of *Gaillardia* named 'Fanfare Citronella' that is distinguishable by a long blooming period, compact, low-growing habit and large inflorescences composed of bright yellow tubular ray florets with a deep orange disc, is disclosed.

2 Drawing Sheets

Genus and species: *Gaillardia×grandiflora.*
Variety denomination: 'Fanfare Citronella'.

BACKGROUND

The present invention relates to a new and distinct cultivar of *Gaillardia* plant, also known as a blanket flower, a herbaceous perennial that is grown for use as an ornamental landscape and container plant. The new variety is known botanically as *Gaillardia×grandiflora* and will be referred to hereinafter by the variety name 'Fanfare Citronella'. *Gaillardia* is in the family Compositae, under which the commonly referred to "flower" is actually the inflorescence, and made up of smaller ray florets and disc florets. The ray florets themselves have the appearance of petals.

'Fanfare Citronella' is product of a *Gaillardia* breeding program started in 2006. The breeding program was conducted in a greenhouse in a nursery environment in West Sussex, United Kingdom. The aims of the breeding program were to produce novel combinations of flower colors and flower forms which are borne on well-branched plants with sturdy growth habits. 'Fanfare Citronella' was selected in 2009 for its bright yellow tubular ray florets which are produced continually from spring until fall and which do not fade with age. 'Fanfare Citronella' was also selected for its compact and naturally branching habit.

'Fanfare Citronella' resulted from the controlled cross pollination in 2008 as follows. The female parent of 'Fanfare Citronella' is an unreleased and unpatented seedling of the inventors' origin, code number 'G719-8' The male parent of 'Fanfare Citronella' is the inventors' variety 'Fanfare Blaze' (U.S. Plant Pat. No. 23,494).

'Fanfare Citronella' was first asexually propagated in September 2009 in an unheated greenhouse at the inventors nursery in West Sussex, United Kingdom using vegetative cuttings. Subsequent asexual propagations have been carried in the same greenhouse using both vegetative cuttings and root cuttings. 'Fanfare Citronella' is stable and reproduces true to type in successive generations of asexual reproduction by either method of asexual propagation.

SUMMARY

The following traits have been repeatedly observed and represent the distinguishing characteristics of 'Fanfare Citronella'. 'Fanfare Citronella' has not been tested under all possible conditions and phenotypic differences may be observed with variations in environmental, climatic, and cultural conditions, without however, any variance in genotype.

1. 'Fanfare Citronella' exhibits a compact and naturally branching plant habit.
2. 'Fanfare Citronella' exhibits large inflorescences composed of numerous bright yellow tubular ray florets.
3. The disc florets of 'Fanfare Citronella' are deep orange in color when the inflorescence is fully expanded.
4. 'Fanfare Citronella' blooms continually from spring until late fall.
5. After one year's growth in a one gallon container, 'Fanfare Citronella' is 50 cm to 55 cm in height and 40 cm to 45 cm in width.
6. 'Fanfare Citronella' is hardy to USDA Zone 5.

DESCRIPTION OF THE PHOTOGRAPHS

The accompanying color photographs illustrate the overall appearance of the new *Gaillardia* cultivar 'Fanfare Citronella' showing the colors as true as it is reasonably possible to obtain in colored reproductions of this type. Colors in the photographs may differ from the color values cited in the detailed botanical description, which more accurately describes the actual colors of the new variety 'Fanfare Citronella'.

DESCRIPTION OF THE NEW VARIETY

Figure 1:
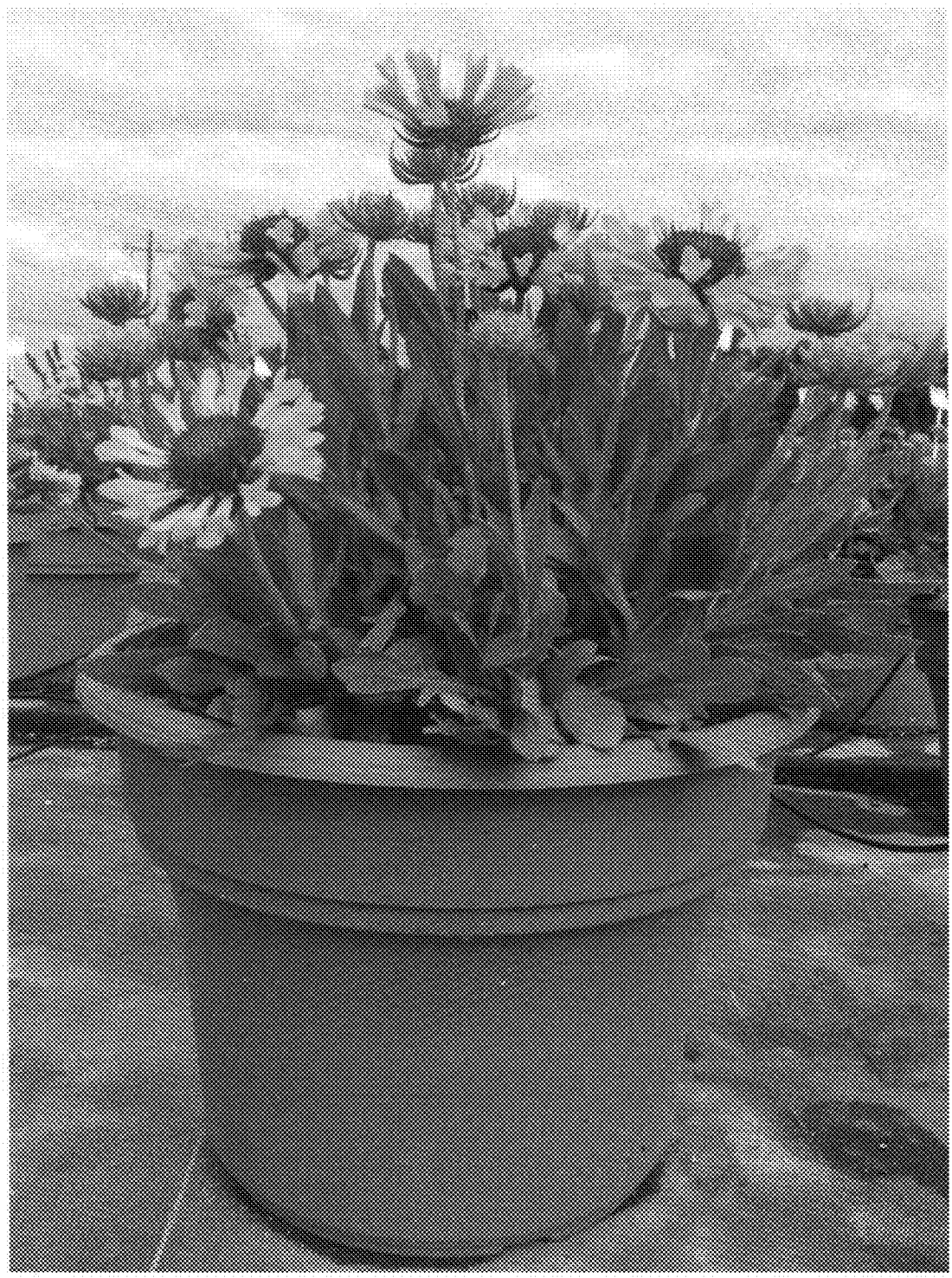
FIG. 1 depicts a whole plant in bud and flower of 'Fanfare Citronella' which has been grown in a frost-free greenhouse in West Sussex, United Kingdom. The illustrated plant is 32 weeks old and has been grown in a 30 cm diameter container without any pinching or chemical growth regulator.
Figure 2:
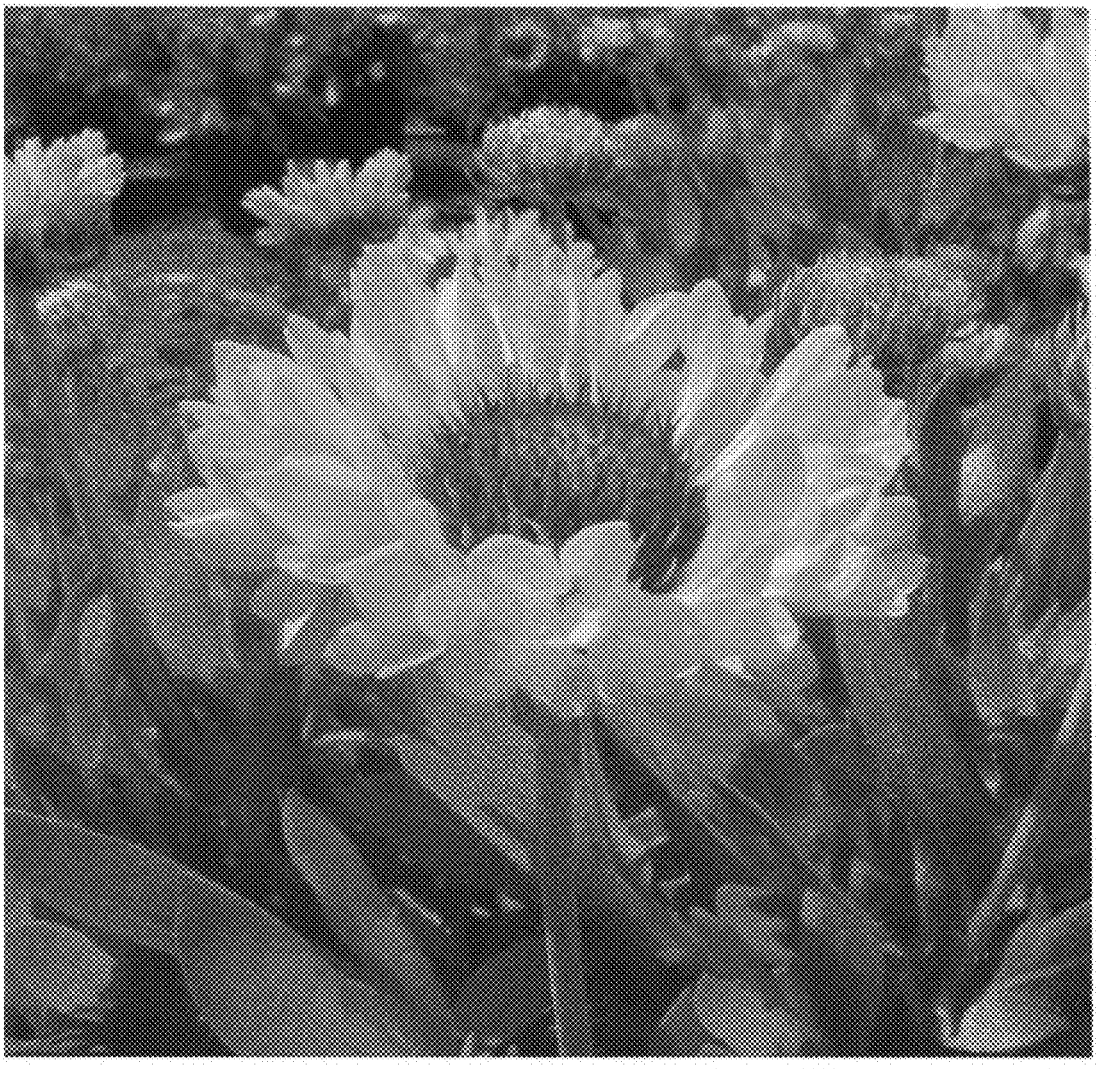
FIG. 2 depicts a close-up view of the fully expanded inflorescence of 'Fanfare Citronella'.

The following detailed descriptions set forth the distinctive characteristics of 'Fanfare Citronella'. Observations, measurements, values, and comparisons were collected in August, 2014 in Santa Barbara, Calif. from a fifteen month old plant grown outdoors in full sun in a 3 gallon container. Color determinations were made in accordance with The 2007 Royal Horticultural Society Colour Chart from London England, except where general color terms of ordinary dictionary significance are used.

Classification:

*Family*.—Compositae.
*Genus*.—*Gaillardia*.
*Species*.—×*grandiflora*.
*Common name*.—Blanket flower.

Parentage:

*Female parent*.—*Gaillardia* code number 'G719-8' (unpatented).
*Male parent*.—*Gaillardia* 'Fanfare Blaze' (U.S. Plant Pat. No. 23,494).

Plant:

*Propagation method*.—Typically by softwood cuttings although root cuttings have also been successful.
*Root system*.—Fine and fibrous.
*Vigor*.—Moderate vigor.
*Time to initiate roots*.—Approximately 14 to 20 days are needed to develop roots on initial cuttings.
*Temperatures to initiate rooting*.—The recommended air temperature is 20-21° Centigrade.
*Crop time*.—Approximately 10 weeks to 2 months are needed to produce a finished 15 cm container plant from a rooted cutting.
*Growth habit*.—Compact and naturally freely branching.
*Suggested container size*.—From 10 cm to 3 gallon.
*Use*.—Ornamental for use as a landscape plant or container plant.
*Type*.—Herbaceous perennial.
*Plant dimensions*.—After one year's growth in a 3 gallon container: 50 cm to 55 cm in height and 40 cm to 45 cm in width.
*Cultural requirements*.—Grow in full sun with moderate water, and well-draining soil such as loam.
*Hardiness*.—USDA Zone 5.
*Growing requirements*.—If grown outside in regions which experience winter freezing, 'Fanfare Citronella' may be started as a cutting during the spring or summer of the previous year, planted out prior to the onset of winter, and flowering will commence typically in May or June according to the region and season.

Stems:

*Stem shape*.—Cylindrical.
*Stem length*.—9 cm to 12 cm.
*Stem diameter*.—5 mm.
*Stem surface*.—Markedly villous with dense coverage of very fine silvery hairs, approximately 2 mm in length.
*Stem color*.—144C.
*Internode length*.—Average internode length is 15 mm to 18 mm.
*Branching habit*.—Basal branching.

Foliage:

*Leaf arrangement*.—Alternate.
*Type*.—Evergreen.
*Leaf shape*.—Predominantly linear with occasional pair of protruding opposite lobes and (rarely) multiple opposite lobes as in an oak leaf.
*Leaf apex*.—Acute.
*Leaf base*.—Strongly attenuate.
*Leaf margins*.—Entire.
*Leaf surface* (*both surfaces*).—Pubescent, very fine silvery hairs, lighter than 202D, approximately 2 mm in length.
*Leaf length*.—22 cm.
*Leaf width*.—1.5 cm (linear leaves), 6.0 cm (at lobes where present).
*Lobes* (*where present as one pair*).—Shape: Bullet. Apex: Rounded. Length: 2.5 cm. Width: 1.0 cm.
*Lobes* (*where present in multiple pairs*).—Shape: Linear. Apex: Acute. Length: 4 cm. Width: 0.75 cm.
*Leaf color* (*both surfaces*).—138A.
*Leaf attachment*.—Sessile.
*Vein pattern*.—Parallel; mid vein protrudes on both surfaces.
*Vein color* (*both surfaces*).—138B.
*Fragrance*.—A slight sage-like scent when bruised.

Inflorescence:

*Form*.—Solitary.
*Aspect*.—Facing upward.
*Dimensions of inflorescence*.—70 mm in diameter and 25 mm in height.
*Type*.—Radiate capitate.
*Shape*—Radiate with center disc.
*Flowering season*.—Spring, summer and fall.
*Fragrance*.—Absent.
*Self-cleaning or persistent*.—Self-cleaning.
*Disc diameter* (*inflorescence fully expanded*).—30 mm.
*Inflorescence number per plant*.—A one-year old plant bears approximately 75 inflorescences in bud and flower at one time.
*Lastingness of inflorescence on the plant*.—10 days, reducing to 7 days in full sun in mid-summer.

Peduncle:

*Length*.—20 cm to 25 cm.
*Diameter*.—3 mm.
*Shape*.—Cylindrical.
*Texture*.—Surface is pubescent and exhibits longitudinal ridges.
*Strength*.—Very stiff and strong.
*Color*.—138C.

Flower buds:

*Surface*.—Villous.
*Height*.—1.50 cm.
*Diameter*.—3 cm.
*Shape*.—Closest to rotate whorl.
*Color*.—138B.

Ray florets:

*Shape*.—Tubular.

*Surface*.—Outer surface: Pubescent. Inner surface: Glabrous.

*Arrangement*.—Radiate.

*Number per inflorescence*.—18 to 21 ray florets per inflorescence.

*Number of petals per ray floret*.—Predominantly four, occasionally three or five.

*Fused or unfused*.—Petals are basally fused.

*Margins*.—Entire.

*Ray floret dimensions*.—3.0 cm in length including the corolla tube, 1.5 cm to 1.8 cm in width at the apex.

*Corolla tube dimensions*.—17 mm in depth and 2 mm to 3 mm in diameter.

*Color*.—Unfused or flared section, both surfaces: 14B. Base where petals fused into a tube, both surfaces: 42A.

*Ray floret veins*.—Upper surface: Longitudinal, parallel, and depressed. Lower surface: Raised. Color (both surfaces): 14B.

Disc florets:

*Quantity per inflorescence*.—Numerous, approximately 200 to 250.

*Disc floret dimensions* (*including pistil length*).—9 mm in length and 2.5 mm in width.

*Corolla tube*.—Comprised of six longitudinally fused petals.

*Depth of disc floret corolla tube*.—6 mm.

*Surface of disc florets*.—Lanate.

*Color of disc florets* (*inflorescence newly opening, both surfaces*).—17C.

*Color of disc florets* (*inflorescence fully expanded, both surfaces*).—N34A.

*Sepals*.—Quantity: 6. Shape: Lanceolate, fused at base. Apex: Aristate. Color: 157D, translucent.

*Phyllary*.—Dimensions: 6 cm in diameter and 1.5 cm in height. Color: 138A. Arrangement: Whorl.

*Involucral bracts*.—Number: An average of 30 per inflorescence. Shape: Oblanceolate. Dimensions: From 35 mm in length and 8 mm in width (lowermost bracts), 15 mm in length and 2.5 mm in width (uppermost bracts). Margin: Entire. Apex: Acute. Base: Truncate. Color (both surfaces): 138A. Surface (both surfaces): Pubescent.

Reproductive organs (present on disc florets only):

*Stamens*.—Quantity: 5, adnate to inner surface of corolla tube. Dimensions: 2 mm in length, 0.25 mm in width. Color: 21B. Form: Plumose. Anthers: Vestigial only. Dimensions: 1 mm in length and 0.5 mm in width. Color: Black, 203A. Shape: Narrow lanceolate. Pollen: Absent.

*Pistil*.—Stigma: Dimensions: 8 mm in length and 1.75 mm in width. Form: Plumose. Color: 187A. Shape: Bifurcate. Ovary: Position: Inferior. Color: 150D. Shape: Globose. Dimensions: 1 mm in width and 2 mm in height.

Fruit/seed set:

*Number of seeds*.—Small to moderate amount (ranges from 50 to 100 seeds per inflorescence).

*Seed dimensions*.—5 mm 6 mm in length (including hairs at apex) and 1 mm to 2 mm in diameter.

*Seed color*.—200A.

*Seed shape*.—Conical with rounded base and apex.

*Seed surface*.—Smooth except at apex where many very fine silver hairs, up to 2 mm in length, are present in circular groups.

Disease and pest susceptibility: 'Fanfare Citronella' has not been observed to exhibit any resistance to any particular pest or disease. 'Fanfare Citronella' is susceptible to downy mildew and to thrips as may be typical of *Gaillardia*.

COMPARISON WITH PARENTAL LINES AND KNOWN VARIETY

'Fanfare Citronella' is distinguishable from the male parent, 'Fanfare Blaze' (U.S. Plant Pat. No. 23,494) as follows. Whereas the male parent exhibits bright orange-red tubular ray florets, the tubular ray florets of 'Fanfare Citronella' are bright yellow in color.

'Fanfare Citronella' is distinguishable from the female parent, 'G719-8' (unpatented) as follows: Whereas the female parent exhibits orange-red tubular ray florets, the ray florets of 'Fanfare Citronella' are also tubular but bright yellow in color. 'Fanfare Citronella' also exhibits a more vigorous growth habit than the female parent.

The closest comparison plant known to the inventor is the inventor's variety, 'Fanfare' (U.S. Plant Pat. No. 15,892). The varieties are similar in respect of their tubular ray florets, however, the tubular ray florets of 'Fanfare' are burnt-orange and orange in color whereas the tubular ray florets of 'Fanfare Citronella' are bright yellow in color. Additionally, 'Fanfare Citronella' exhibits more vigorous growth and a longer flowering period.

We claim:

1. A new and distinct cultivar of *Gaillardia* plant named 'Fanfare Citronella' as described and illustrated herein.

* * * * *